United States Patent
Bystrom et al.

(10) Patent No.: US 9,061,016 B2
(45) Date of Patent: Jun. 23, 2015

(54) AQUEOUS SOLUTION COMPRISING 3-QUINUCLIDINONES FOR THE TREATMENT HYPERPROLIFERATIVE, AUTOIMMUNE AND HEART DISEASE

(75) Inventors: Styrbjorn Bystrom, Taby (SE); Charlotta Liljebris, Knivsta (SE); Ninus Caram-Lelham, Uppsala (SE)

(73) Assignee: APREA AB, Solna (SE)

( * ) Notice: Subject to any disclaimer, the term of this patent is extended or adjusted under 35 U.S.C. 154(b) by 0 days.

(21) Appl. No.: 13/521,841

(22) PCT Filed: Jan. 21, 2011

(86) PCT No.: PCT/EP2011/050854
§ 371 (c)(1),
(2), (4) Date: Jul. 12, 2012

(87) PCT Pub. No.: WO2011/089234
PCT Pub. Date: Jul. 28, 2011

(65) Prior Publication Data
US 2012/0289503 A1   Nov. 15, 2012

Related U.S. Application Data

(60) Provisional application No. 61/296,964, filed on Jan. 21, 2010.

(30) Foreign Application Priority Data

Jan. 21, 2010   (EP) .................................... 10151326

(51) Int. Cl.
| | |
|---|---|
| A61K 31/535 | (2006.01) |
| A61K 31/497 | (2006.01) |
| A61K 31/519 | (2006.01) |
| A61K 31/517 | (2006.01) |
| A61K 31/44 | (2006.01) |
| A61K 31/439 | (2006.01) |
| A61K 9/00 | (2006.01) |
| A61K 9/08 | (2006.01) |
| A61K 31/444 | (2006.01) |
| A61K 31/496 | (2006.01) |
| A61K 31/522 | (2006.01) |
| A61K 31/5377 | (2006.01) |

(52) U.S. Cl.
CPC .............. *A61K 31/439* (2013.01); *A61K 9/0019* (2013.01); *A61K 9/08* (2013.01); *A61K 31/444* (2013.01); *A61K 31/496* (2013.01); *A61K 31/519* (2013.01); *A61K 31/522* (2013.01); *A61K 31/5377* (2013.01)

(58) Field of Classification Search
USPC .......... 514/233.2, 253.04, 261.1, 263.22, 305
See application file for complete search history.

(56) References Cited

U.S. PATENT DOCUMENTS

| | | | | |
|---|---|---|---|---|
| 3,775,418 | A * | 11/1973 | Potoski et al. ................... | 546/16 |
| 7,659,278 | B2 * | 2/2010 | Bykov et al. ............... | 514/261.1 |
| 2009/0215903 | A1 | 8/2009 | Munoz et al. | |

FOREIGN PATENT DOCUMENTS

| | | |
|---|---|---|
| JP | 2004-509890 A | 4/2004 |
| JP | 2007269786 A | 10/2007 |
| JP | 2007-530534 A | 11/2007 |
| JP | 2008001606 A | 1/2008 |
| JP | 2008201778 A | 9/2008 |
| JP | 2009046490 A | 3/2009 |
| JP | 2009-543851 A | 12/2009 |
| WO | 02/024692 A1 | 3/2002 |
| WO | 02083079 A2 | 10/2002 |
| WO | 03/070250 A1 | 8/2003 |
| WO | 2004/084893 A1 | 10/2004 |
| WO | 2005/090341 A1 | 9/2005 |
| WO | 2008104595 A1 | 9/2008 |

OTHER PUBLICATIONS

Shi H et al.: "In vitro and in vivo cytotoxic effects of PRIMA-I on hepatocellular carcinoma cells expressing mutant p53ser249", Carci Nogenesi s, Oxford University Press, GB, vol. 29, No. 7, Nov. 18, 2007, pp. 1428-1434, XP009134458, ISSN: 0143-3334 abstract p. 1429, left-hand column, paragraph In vivo assay p. 1430, right-hand column, paragraph In vitro antitumor effect . . . ; figure 2c.
International Search Report, dated Aug. 12, 2011, from corresponding PCT application.
Russian Office Action, dated Jan. 26, 2015, in corresponding Russian Patent Application No. 2012135698, with partial English translation.
Chueshov, V.I., "Promyshlennaya technologia lekarstv (Industrial drug technology). vol. 2", Kn.: MTK-Kniga, 2002, pp. 62-63, discussed in English on p. 6 of the English translation of the Russian Office Action.
Jeremy M.R. Lambert, et al. "PRIMA-1 Reactivates Mutant p53 by Covalent Binding to the Core Domain," Cancer Cell 15, 376-388, May 5, 2009.
Muraviev, I.A. Teknologia lekarstv (Drug technology). vol. II, 1980, pp. 617, 638-639, 677-678, discussed in English on p. 6 of the English translation of the Russian Office Action.
Japanese Office Action, dated Apr. 6, 2015, in corresponding Japanese Application No. 2012-549372, with partial English Translation.
Nippon Rinsho (Clinic in Japan)(supplement), "Manual of Recent Drug Therapies," Jun. 24, 1991, vol. 49, pp. 121-124.
"Overview of Pharmaceutics, Introduction to Modern Pharmaceutics," 1980, Nankodo, Inc., 3rd edition, pp. 345-372.

* cited by examiner

*Primary Examiner* — Shirley V Gembeh
(74) *Attorney, Agent, or Firm* — Young & Thompson

(57) ABSTRACT

A liquid composition that is an aqueous solution of a compound of formula (I), wherein the aqueous solution has a pH from about 3.0 to about 5.0. The liquid composition may be used in the treatment of a disorder selected from hyperproliferative diseases, autoimmune diseases and heart diseases.

19 Claims, 1 Drawing Sheet

AQUEOUS SOLUTION COMPRISING 3-QUINUCLIDINONES FOR THE TREATMENT HYPERPROLIFERATIVE, AUTOIMMUNE AND HEART DISEASE

FIELD OF THE INVENTION

The present invention relates to a formulation of a quinuclidinone derivative and to a method of preparing such formulation, as well as to the use of such formulation.

BACKGROUND OF THE INVENTION 3-quinuclidinone derivatives for use in the treatment of various disorders, e.g. hyperproliferative diseases, autoimmune diseases and heart diseases are described in WO05/090341. Similarly, 3-quinuclidinone derivatives for use especially in the treatment of tumor diseases are disclosed in WO04/084893, WO02/024692 and WO03/070250.

In WO05/090341 it is mentioned that a composition of the quinuclidinones disclosed therein may be prepared for any route of administration, e.g. oral, intravenous, cutaneous or subcutaneous, nasal, intramuscular, or intraperitoneal and that the precise nature of the carrier or other material will depend on the route of administration. It also is noted that for a parenteral administration, a parenterally acceptable aqueous solution is employed, which is pyrogen free and has requisite pH, isotonicity and stability.

However, the present inventors found that in a liquid aqueous solution, such as one useful for parenteral administration (i.e. generally having a pH of 6.5-7.5) or the corresponding stock solution for preparing a parenterally administrable solution, the inventive compounds had an unacceptably low stability, forming degradation products within only a few hours after solubilization. This lack of chemical stability in a liquid solution was quite unexpected for the compounds described in the above-mentioned prior art documents.

SUMMARY OF THE INVENTION

One object according to the present invention is to provide a formulation of 3-quinuclidinone derivatives as defined herein, having an improved shelf life, in particular compared to prior art formulations.

Another object according to the invention is to provide a formulation of improved shelf life comprising 3-quinuclidinone derivatives as defined herein, that are useful in therapy; e.g. in the treatment of a disorder selected from hyperproliferative diseases, e.g. cancer, autoimmune diseases and heart diseases, said formulation having an improved shelf life, in particular compared to prior art formulations.

Still another object is to provide a liquid formulation containing a 3-quinuclidinone derivative as defined herein, wherein the 3-quinuclidinone derivative has a reduced degradation rate.

A further object of the invention is to provide a pharmaceutical formulation for the treatment of hyperproliferative diseases, autoimmune diseases and heart diseases, said formulation containing a 3-quinuclidinone derivative as defined herein below and having an improved shelf life, in particular compared to prior art formulations.

A further object of the invention is to provide a formulation allowing for prolonged storage of a 3-quinuclidinone derivative as defined herein.

Another object of the invention is to provide a method for preparing a formulation according to the invention.

In one particular embodiment, the present invention provides a formulation that is an aqueous solution of a 3-quinuclidinone derivative according to formula (I)

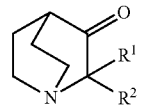

wherein:
$R^1$ is selected from H, —$CH_2$—O—$R^3$, —$CH_2$—S—$R^3$, and —$CH_2$—$NR^3R^4$;
$R^2$ is selected from —$CH_2$—O—$R^3$, —$CH_2$—S—$R^3$, and —$CH_2$—$NR^3R^4$;
$R^3$ and $R^4$ are the same or different and are independently selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C2-C10 heteroaryl or non-aromatic C2-C10 heterocyclyl containing one or several heteroatoms independently selected from N, O and S; or $R^3$ and $R^4$ in —$CH_2$—$NR^3R^4$ are bonded together and form, together with the nitrogen atom to which they are bonded, a substituted or non-substituted non-aromatic C2-C10 mono- or bicyclic heterocyclyl optionally containing one or several further heteroatoms independently selected from N, O and S and optionally comprising one or several cyclic keto groups;
wherein the substituents of the substituted groups are independently selected from unbranched or branched, saturated or unsaturated C3-C12 cycloalkyl or C1-C10 alkyl; halogen; halogen-substituted C1-C10 alkyl, mono- or bicyclic aryl; mono-, bi- or tricyclic C2-C10 heteroaryl or non-aromatic C2-C10 heterocyclyl containing one or several heteroatoms independently selected from N, O and S; C1-C10 alkoxy; amino; and C1-C10 alkylamino;
or a pharmaceutically acceptable salt thereof,
and at least one pH regulating agent in an amount such as to provide a pH in the aqueous solution of from about 3.0 to about 5.0.

In one embodiment, the formulation is a pharmaceutical formulation. Thus, there is provided a liquid formulation as defined herein for use in therapy.

In one embodiment, the formulation is a stock solution allowing long-term storage of a 3-quinuclidinone derivative of formula (I) dissolved therein.

In one embodiment, the 3-quinuclidinone derivative of formula (I) comprised in the formulation of the invention is useful in the treatment of a disorder selected from hyperproliferative diseases, such as cancer, autoimmune diseases and heart diseases, in particular in the treatment of cancer.

In one further embodiment, there is provided a liquid formulation of a 3-quinuclidinone derivative as defined herein for use in a method for the prevention and/or treatment of a pathophysiological condition, e.g. a hyperproliferative disease, such as cancer, an autoimmune disease or a heart disease.

Another embodiment relates to the use of a liquid formulation of a 3-quinuclidinone as defined herein for the manufacturing of a medicament for the prevention and/or treatment of a pathophysiological condition, e.g. a hyperproliferative disease, such as cancer, an autoimmune disease or a heart disease.

In one further embodiment, a method for the prevention and/or treatment of a pathophysiological condition is provided which comprises the administration, preferably the parenteral administration, of an effective amount of a composition of the present invention, to a mammal in need thereof.

In one further embodiment, a method for the prevention and/or treatment of a pathophysiological condition is provided which comprises the administration, preferably the parenteral administration, of an effective amount of a composition prepared by use of a liquid formulation according to the present invention to a mammal in need thereof.

Furthermore, a method for the prevention and/or treatment of a pathophysiological condition mediated by abnormal cell growth is provided which comprises administering, parenterally or orally, an effective amount of a composition of the present invention or a composition prepared by use of a liquid formulation according to the present invention, to a mammal.

In one particular embodiment, a method for the prevention and/or treatment of a pathophysiological condition mediated by abnormal cell growth is provided which comprises administering, parenterally or orally, an effective amount of a composition of the present invention to a mammal in need of therapeutic intervention to control the pathophysiological condition and wherein abnormal cell growth is controlled.

A method for preparing the liquid formulation of the invention also is provided, comprising adding to an aqueous phase, a compound of formula (I), or a pharmaceutically acceptable salt thereof, optionally at least one further therapeutically active agent, and a pH regulating agent in an amount so as to provide a pH in the composition of from 3.0 to 5.0.

Further embodiments of the invention are as described herein below and as defined in the claims.

DETAILED DESCRIPTION OF THE INVENTION

Figure 1:
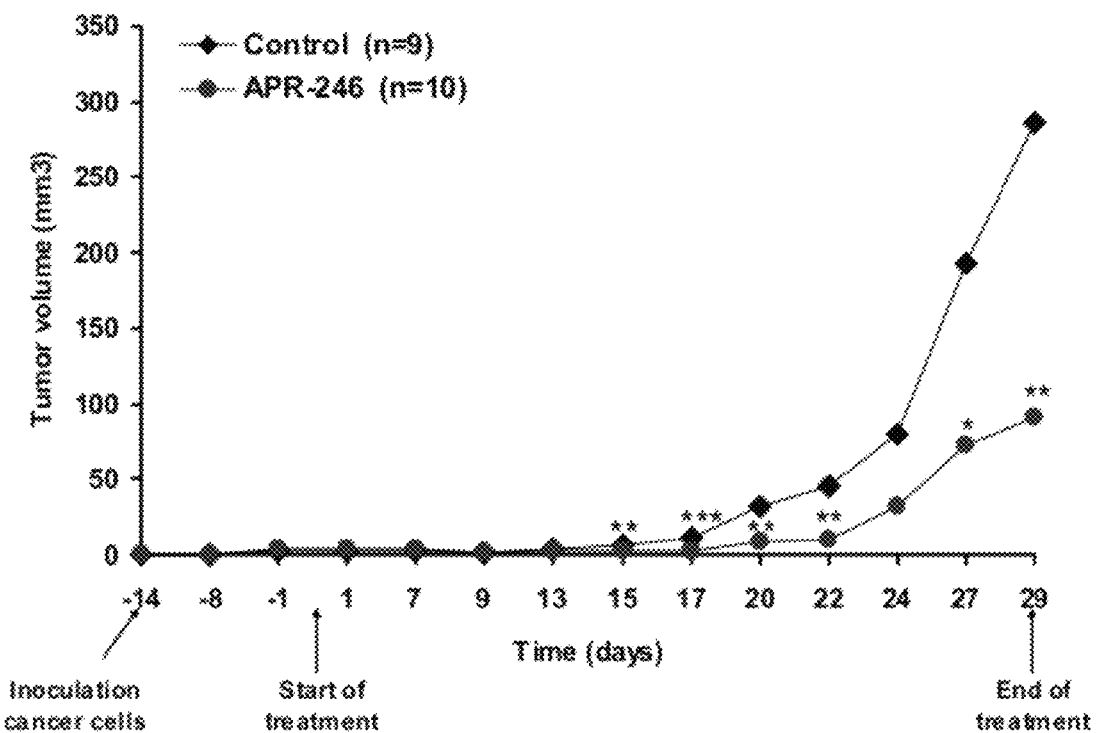
FIG. 1 shows the volume of p53 mutant xenograft tumors in SCID mice, treated intravenously with 2-(hydroxymethyl)-2-(methoxymethyl)quinuclidin-3-one (APR-246) or with PBS (the vehicle, control), at a dosage of 100 mg/kg, twice a day, 3-4 days/week. As can be seen, at the end of the treatment period, the mean tumor volume in control animals was more than three times as high as that in animals treated with APR-246. Differences in tumor volumes were analyzed using Mann-Whitney test. A statistically significant anti-cancer effect was found.

Unless defined otherwise, all technical and scientific terms used herein have the same meaning as is commonly understood by one skilled in the art to which this invention belongs.

Thus, unless otherwise indicated, a "stock solution" refers to a generally concentrated solution that will be diluted to some lower concentration for actual use. As is known to the person of ordinary skill in the art, stock solutions are used e.g. to save preparation time, conserve materials, reduce storage space, and improve the accuracy with which working solutions are prepared.

By "shelf life" is meant the length of time a product may be stored without becoming unsuitable for use or consumption.

In accordance with the present invention it has surprisingly been found that in an aqueous solution having a pH of at most about 5.0, the chemical stability of the 3-quinclidinones as referred to herein above is substantially increased. Indeed, it has been found that in some cases, the rate of degradation decreases by a factor of more than $10^3$ as compared to corresponding solutions at higher pH.

Consequently, the present invention provides a composition comprising an aqueous solution of a 3-quinuclidinone derivative as defined herein, wherein the aqueous solution has a pH of from about pH 3.0 to about pH 5.0, preferably to about 4.7, or to about 4.5, or to about 4.2, e.g. to about 4.0. For example, the pH may range between a lower limit of pH 3.0 or pH 3.5 and an upper limit of pH 5 or pH 4.5, and preferably may be in a range between pH 3.8 and pH 4.2, e.g. being approximately 4.0. For example, the pH of the aqueous solution of the invention may have a lower limit selected from a pH of about 3.0, or about 3.2, e.g. about 3.4, such as about 3.6 or about 3.8, and an upper limit of about 5.0, or about 4.7, or about 4.5, or about 4.2, e.g. about 4.0.

At the pH of the invention, the chemical stability against degradation of the 3-quinuclidinone derivative of formula (I) dissolved in the aqueous solution of the invention is substantially improved, compared to the stability of the compound in an aqueous solution according to the prior art. In fact, an aqueous solution of a 3-quinuclidinone derivative according to the invention may have a shelf life of 24 months, or even longer, at 2-8° C.

The 3-quinuclidinone derivative present in the inventive formulation is a compound according to formula (I)

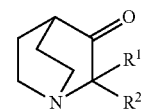

I wherein:
$R^1$ is selected from H, —$CH_2$—O—$R^3$, —$CH_2$—S—$R^3$, and —$CH_2$—$NR^3R^4$;
$R^2$ is selected from —$CH_2$—O—$R^3$, —$CH_2$—S—$R^3$, and —$CH_2$—$NR^3R^4$;
$R^3$ and $R^4$ are the same or different and are independently selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C2-C10 heteroaryl or non-aromatic C2-C10 heterocyclyl containing one or several heteroatoms independently selected from N, O and S; or $R^3$ and $R^4$ in —$CH_2$—$NR^3R^4$ are bonded together and form, together with the nitrogen atom to which they are bonded, a substituted or non-substituted non-aromatic C2-C10 mono- or bicyclic heterocyclyl optionally containing one or several further heteroatoms independently selected from N, O and S and optionally comprising one or several cyclic keto groups;
wherein the substituents of the substituted groups are independently selected from unbranched or branched, saturated or unsaturated C3-C12 cycloalkyl or C1-C10 alkyl; halogen; halogen-substituted C1-C10 alkyl, mono- or bicyclic aryl; mono-, bi- or tricyclic C2-C10 heteroaryl or non-aromatic C2-C10 heterocyclyl containing one or several heteroatoms independently selected from N, O and S; C1-C10 alkoxy; amino; and C1-C10 alkylamino;
or a pharmaceutically acceptable salts thereof.

The pharmaceutically acceptable salt of the compound of formula (I) e.g. may be an acid addition salt of an inorganic mineral acid or of an organic acid.

In a compound of formula (I), $R^1$ is selected from H, —$CH_2$—O—$R^3$, —$CH_2$—S—$R^3$, and —$CH_2$—$NR^3R^4$.

In some embodiments, $R^1$ is selected from H, —$CH_2$—O—$R^3$, and —$CH_2$—S—$R^3$. In some embodiments, $R^1$ is selected from H and —$CH_2$—O—$R^3$. In other embodiments, $R^1$ is selected from —$CH_2$—O—$R^3$, and —$CH_2$—S—$R^3$. In some embodiments, $R^1$ is H.

$R^2$ in formula (I) is selected from —$CH_2$—O—$R^3$, —$CH_2$—S—$R^3$, and —$CH_2$—$NR^3R^4$. In some embodiments, $R^2$ is selected from —$CH_2$—O—$R^3$ and —$CH_2$—S—$R^3$. In still other embodiments, $R^2$ is —$CH_2$—O—$R^3$.

In one embodiment, $R^1$ is selected from H, —$CH_2$—O—$R^3$ and —$CH_2$—S—$R^3$; and $R^2$ is selected from —$CH_2$—O—$R^3$ and —$CH_2$—S—$R^3$.

In one embodiment, $R^1$ is H; and $R^2$ is selected from —$CH_2$—O—$R^3$, —$CH_2$—S—$R^3$ and —$CH_2$—$NR^3R^4$; e.g. from —$CH_2$—O—$R^3$ and —$CH_2$—S—$R^3$, and in particular is —$CH_2$—O—$R^3$.

In one embodiment, $R^1$ is selected from H and —$CH_2$—O—$R^3$; and $R^2$ is —$CH_2$—O—$R^3$.

In one embodiment, both $R^1$ and $R^2$ are —$CH_2$—O—$R^3$.

In one embodiment, each $R^3$ is independently selected from H; substituted or non-substituted, unbranched or branched, saturated or unsaturated C3-C12 cycloalkyl and C1-C10 alkyl, and benzyl. For example, each $R^3$ may be independently selected from H and C1-C10 alkyl, e.g. from H and C1-C6 alkyl, from H and C1-C4 alkyl, or from H and C1-C3 alkyl, in particular from H and methyl.

In one embodiment, $R^1$ is selected from H and —$CH_2$—O—$R^3$, and $R^2$ is —$CH_2$—O—$R^3$, and each $R^3$ is independently selected from H; substituted or non-substituted, unbranched or branched, saturated or unsaturated C3-C12 cycloalkyl and C1-C10 alkyl, and benzyl, in particular from H and C1-C10 alkyl, e.g. from H and C1-C6 alkyl, from H and C1-C4 alkyl, or from H and C1-C3 alkyl, in particular from H and methyl.

In one embodiment, $R^1$ and $R^2$ are both —$CH_2$—O—$R^3$, and each $R^3$ is independently selected from H; substituted or non-substituted, unbranched or branched, saturated or unsaturated C3-C12 cycloalkyl and C1-C10 alkyl; in particular from H and C1-C10 alkyl; e.g. from H and C1-C6 alkyl, from H and C1-C4 alkyl, or from H and C1-C3 alkyl, in particular from H and methyl.

In a compound of formula (I), as defined herein above, any C1-C10 alkyl e.g. may be a C1-C6 alkyl, or a C1-C4 alkyl, e.g. methyl, ethyl, propyl or butyl. Any C3-C12 cycloalkyl may be e.g. a C3-C8 cycloalkyl, or a C3-C6 cycloalkyl. Any mono- or bicyclic aryl may be e.g. a monocyclic aryl, such as phenyl. Any mono-, bi- or tricyclic C2-C10 heteroaryl may be e.g. a monocyclic or bicyclic C2-C5 heteroaryl, e.g. a 5- or 6-membered monocyclic or a 9-membered bicyclic C2-C5 heteroaryl. Any mono-, bi- or tricyclic non-aromatic C2-C10 heterocyclyl may be e.g. a monocyclic or bicyclic C2-C5 heterocyclyl, e.g. a 5- or 6-membered monocyclic or 9- or 10-membered bicyclic C2-C5 heterocyclyl. Any halogen may be selected from F, Cl, Br and I, preferably from F and Cl. Any heterocycle, aromatic or not, containing one or several heteroatoms independently selected from N, O and S, e.g. may contain 1-5 heteroatoms, e.g. independently selected from N and O.

In one embodiment, in a compound of formula (I) as defined herein above, any substituted or non-substituted C3-C12 cycloalkyl or C1-C10 alkyl is non-substituted.

In one embodiment, any substituted or non-substituted benzyl is non-substituted.

In one embodiment, any substituted or non-substituted mono- or bicyclic aryl is non-substituted.

In one embodiment, any substituted or non-substituted mono-, bi- or tricyclic C2-C10 heteroaryl or non-aromatic C2-C10 heterocyclyl is non-substituted.

In one embodiment, when any of the above groups is substituted, each substituent is selected from C1-C10 alkyl, e.g. C1-C6 alkyl, C1-C4 alkyl, or C1-C3 alkyl, such as methyl; halogen, e.g. Cl; halogen-substituted C1-C10 alkyl, e.g. trifluoromethyl; monocyclic C2-C5 heteroaryl, e.g. pyridyl; C1-C10 alkoxy, e.g. C1-C6 alkoxy, C1-C4 alkoxy, or C1-C3 alkoxy, such as methoxy; and amino.

In one embodiment, when any of the above groups is substituted, the number of substituents on each substituted group is 1, 2 or 3.

In another embodiment, the 3-quinuclidinone derivative of the invention is selected from those exemplified in the prior art documents referred to herein above, e.g. WO05/090341, WO04/084893, WO02/024692 and WO03/070250, e.g. as represented in Table 1:

TABLE 1

Compounds of formula (I)

| Structural formula | Chemical name |
|---|---|
|  | 2-(hydroxymethyl)-2-(methoxymethyl)quinuclidin-3-one |
|  | 2,2-bis(hydroxymethyl)quinuclidin-3-one |
|  | 2-[(benzyloxy)methyl]quinuclidin-3-one |
|  | 2-(butoxymethyl)quinuclidin-3-one |
|  | 2-(propoxymethyl)quinuclidin-3-one |
|  | 2-[(phenylthio)methyl]quinuclidin-3-one |
|  | 2-[(7H-purin-6-ylthio)methyl]quinuclidin-3-one |

TABLE 1-continued

Compounds of formula (I)

| Structural formula | Chemical name |
|---|---|
| 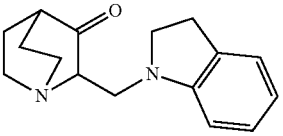 [SMILES: O=C1C2CCN(CC2)C1CN1CCc2ccccc21] | 2-(2,3-dihydro-1H-indol-1-ylmethyl)quinuclidin-3-one |
| 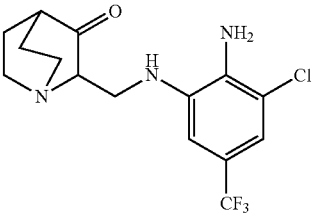 [SMILES: Nc1c(Cl)cc(C(F)(F)F)cc1NCC1C(=O)C2CCN1CC2] | 2-({[2-amino-3-chloro-5-(trifluoromethyl)phenyl]-amino}methyl)quinuclidin-3-one |
| 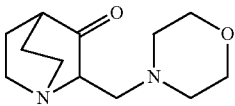 [SMILES: O=C1C2CCN(CC2)C1CN1CCOCC1] | 2-(morpholin-4-ylmethyl)quinuclidin-3-one |
| 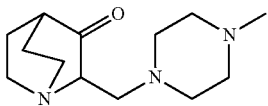 [SMILES: CN1CCN(CC2C(=O)C3CCN2CC3)CC1] | 2-[(4-methylpiperazin-1-yl)methyl]quinuclidin-3-one |
| 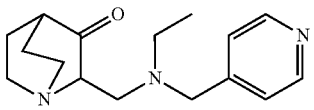 [SMILES: CCN(Cc1ccncc1)CC1C(=O)C2CCN1CC2] | 2-{[ethyl(pyridin-4-ylmethyl)amino]methyl}quinuclidin-3-one |
| 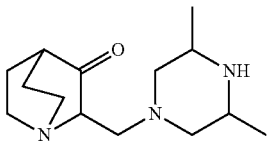 [SMILES: CC1CN(CC2C(=O)C3CCN2CC3)CC(C)N1] | 2-[(3,5-dimethylpiperazin-1-yl)methyl]quinuclidin-3-one |
| 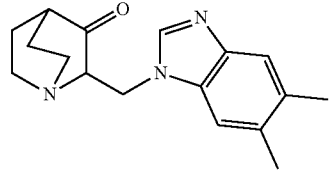 [SMILES: Cc1cc2ncn(CC3C(=O)C4CCN3CC4)c2cc1C] | 2-[(5,6-dimethyl-1H-benzimidazol-1-yl)methyl]-quinuclidin-3-one |
| 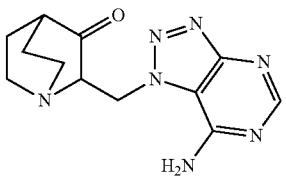 [SMILES: Nc1ncnc2nnn(CC3C(=O)C4CCN3CC4)c12] | 2-[(7-amino-1H-[1,2,3]triazolo[4,5-d]pyrimidin-1-yl)methyl]quinuclidin-3-one |
| 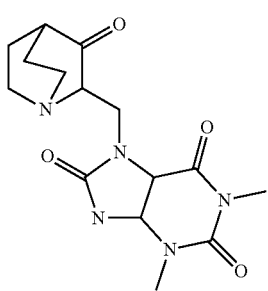 [SMILES: CN1C(=O)C2C(NC(=O)N2CC2C(=O)C3CCN2CC3)N(C)C1=O] | 1,3-dimethyl-7-[(3-oxo-1-azabicyclo[2.2.2]oct-2-yl)methyl]tetrahydro-1H-purine-2,6,8(3H)-trione |

TABLE 1-continued

Compounds of formula (I)

| Structural formula | Chemical name |
|---|---|
| 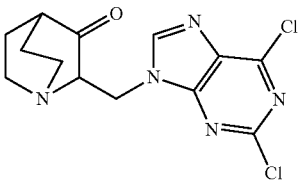 [SMILES: O=C1C2CCN(CC2)C1Cn1cnc2c(Cl)nc(Cl)nc21] | 2-[(2,6-dichloro-9H-purin-9-yl)methyl]quinuclidin-3-one |
| 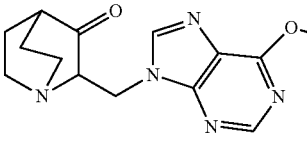 | 2-[(6-methoxy-9H-purin-9-yl)methyl]quinuclidin-3-one |

In one embodiment, the 3-quinuclidinone derivative of the invention, i.e. the compound of formula (I), is selected from 2-(hydroxymethyl)-2-(methoxymethyl)quinuclidin-3-one and 2,2-bis(hydroxymethyl)quinuclidin-3-one, and pharmaceutically acceptable salts of these compounds.

In one embodiment, the compound of formula (I) is 2-(hydroxymethyl)-2-(methoxymethyl)quinuclidin-3-one or a pharmaceutically acceptable salt thereof.

In another embodiment, the compound of formula (I) is 2,2-bis(hydroxymethyl)quinuclidin-3-one or a pharmaceutically acceptable salt thereof.

In one embodiment, the formulation is a stock solution and preferably is a pharmaceutical formulation in the form of a concentrated stock solution. The formulation preferably is sterile, and this may be achieved by known sterilization methods such as filtration, allowing for long term storage essentially without any deterioration of the compound of the invention, e.g. by a chemical reaction of degradation, and essentially without formation of degradation products.

The formulation according to the invention can be used e.g. for administration to a patient in need thereof by direct injection or preferentially diluted with appropriate injectable solutions for i.v. infusion.

The formulation according to the invention also may be used, as such or diluted, e.g. for further research on the 3-quinuclidinone derivative contained therein, such as by in vitro or in vivo tests, e.g. by administration to a laboratory animal, such as a mouse, a rat, a rabbit, or a dog.

In one embodiment, the formulation according to the invention is an aqueous solution of the 3-quinuclidinone derivative of formula (I) as defined herein, wherein said derivative is present at a concentration within a range of about 10 mg/mL to about 250 mg/mL, particularly in a range of about 50 mg/mL to about 200 mg/mL, and especially in a range of about 75 mg/mL to about 150 mg/mL of the formulation.

The formulation of the present invention may be diluted prior to use, e.g. administration to a patient. The dilution factor depends on the concentration of the 3-quinuclidinone derivative in the formulation and the required amount of the compound needed, e.g. to meet the therapeutically effective dose. In case of parenteral administration, the final diluted product preferably should have a pH within the range of about pH 4 to about pH 6, more preferably the final diluted product for parenteral administration should have a pH within the range of about pH 4.2 to about pH 5.5.

The liquid formulation may contain sodium chloride at a concentration of between 0% and 3%, particularly in a concentration of between 0.5% and 1.5%, but especially in a concentration of between 0.8% and 1% weight by volume of the formulation.

In one embodiment of the invention, the 3-quinuclidinone is present in the liquid formulation in the form of an acid addition salt with one or several different pharmaceutically acceptable acids. The pharmaceutically acceptable acid may be a mineral acid, e.g. selected from the group consisting of hydrochloric acid, hydrogen bromide, hydrogen iodide, sulphuric acid, nitric acid, phosphoric acid and the like. As an alternative, the pharmaceutically acceptable acid may be an organic acid, e.g. a sulfonic or carboxylic acid, particularly an alkyl or aryl sulfonic acid or an alkyl or aryl carboxylic acid, such as selected from the group consisting of methanesulfonic acid, p-toluenesulfonic acid, benzenesulfonic acid, acetic acid, tartaric acid, maleic acid, citric acid, benzoic acid, salicylic acid, ascorbic acid and the like.

In order to be at the required pH, the composition of the invention contains a pH regulating agent. By the term pH regulating agent, as used herein, is meant at least one pharmaceutically acceptable organic or inorganic (mineral) acid, or at least one pharmaceutically acceptable acid buffer or a mixture of any of these. Thus, the pH regulating agent may be any such acid or buffer, or a mixture of acids or buffers, or a mixture of acid(s) and buffer(s). Examples of useful acids and buffers are as indicated herein.

For example, the composition according to the invention may contain at least one pharmaceutically acceptable acid. The acid may be an inorganic mineral acid, e.g. selected from the group consisting of hydrochloric acid, hydrobromic acid, hydroiodic acid, sulphuric acid, nitric acid, phosphoric acid or the like, or an organic acid, e.g. selected from the group consisting of acetic acid, succinic acid, tartaric acid, maleic acid, ascorbic acid, citric acid, glutamic acid, benzoic acid, ascorbic acid, methanesulfonic acid, ethanesulfonic acid and the like. It is contemplated that the composition may contain one or several acids, selected from inorganic and organic acids. In one embodiment, the required pH of the formulation is achieved by addition of hydrochloric acid.

The composition of the invention also may comprise at least one pharmaceutically acceptable buffer, particularly selected from the group of citric buffer, acetate buffer, phosphate buffer and the like, separately or as a mixture thereof, as well as in combination with any pharmaceutically acceptable acid, as defined herein, e.g. hydrochloric acid.

The liquid composition of the invention is aqueous, which means that it contains water. However, it is contemplated that the aqueous solution and the aqueous phase used to prepare the inventive composition also may contain other pharmaceutically acceptable liquids as a solvent phase, e.g. polyethylene glycol (PEG) and alcohols, e.g. ethanol. Preferably, though, the agueous phase mainly comprises water as a solvent. For example, the solvent phase is comprised of from 50 to 100% water, more preferably at least 80% water, or at least 90% water, at least 95% water, at least 98% water or 100% water.

In one embodiment, the composition according to the invention as described herein is provided as a stable stock solution, particularly as a concentrated stock solution for long term storage at a temperature range of 2-8° C., in a container, particularly a sealed and sterilized container. For example, the composition may comprise a stable aqueous WFI (water for injection) solution of the compound of the invention, optionally as an acid addition salt, in particular a hydrochloride addition salt, in a concentration of at about 10 mg/mL to about 250 mg/mL, particularly in a range of about 50 mg/mL to about 200 mg/mL, but especially in a range of about 75 mg/mL to about 150 mg/mL, and a pH regulating agent in such an amount as to provide a pH in the solution in a range of between pH 3.0 and pH 5.0, particularly in the range of between pH 3.2 and pH 4.7, e.g. between pH 3.5 and pH 4.5, especially in a range between pH 3.8 and pH 4.2, e.g. approximately 4.0. For example, the pH of the stock solution may have a lower limit selected from a pH of about 3.0, or about 3.2, e.g. about 3.4, such as about 3.6 or about 3.8, and an upper limit of about 5.0, or about 4.7, or about 4.5, or about 4.2, e.g. about 4.0.

The present invention also provides a method for preparing a formulation of a compound according to the invention. Generally, the method comprises admixing a compound of formula (I), or a pharmaceutically acceptable salt thereof, and a pH regulating agent, with an aqueous phase. In this method, the pH of the aqueous phase is adjusted to a desired range by adding the pH regulating agent, as defined herein, either before or after adding the compound of formula (I). For example, the pH of the aqueous phase is adjusted to a pH below pH 6, e.g. below pH 5 or below pH 4.5, before adding the compound of formula (I), whereafter the compound of formula (I) is added. The pH may then be adjusted again, so as to ensure that the composition is at the desired value according to the invention. However, even if less preferred, the compound of formula (I) also may be added to the aqueous phase before adding any pH regulating agent, and subsequently the pH of the liquid formulation is adjusted to the desired range by adding the pH regulating agent.

Preferably, the pH of the liquid phase is maintained at below 6, e.g. below 5.0 or below 4.5, e.g. within the range from 3.0 to 6.0, during the major part of the process of preparation, and more preferably during the whole process of preparation.

In one embodiment, the method of preparing a liquid formulation of the invention comprises preparing an aqueous phase having a pH below pH 6.0, and admixing a compound of formula (I) in incremental portions, with addition of incremental portions of pH regulating agent, if necessary, so as to maintain the pH of the liquid formulation below pH 6.0, e.g. below pH 5, or below pH 4.5, during preferably the whole process of preparation.

The pH of the aqueous formulation may be measured continuously or intermittently during the preparation process.

Other components also may be added to or present in the aqueous phase, such as pharmaceutically acceptable inorganic salts, e.g. NaCl, preservatives, or further pharmaceutically acceptable compounds, e.g. further therapeutically active ingredients, such as cytostatics, particularly cisplatin, daunorubicin, cerubidine, cytarabine and fludarabine.

In one embodiment, NaCl is added to the aqueous phase in an amount so as to provide a final liquid composition as defined herein above, containing NaCl at a concentration of between 0% and 3%, particularly in a concentration of between 0.5% and 1.5%, but especially in a concentration of between 0.8% and 1% weight by volume of the formulation.

In one embodiment the composition according to the invention is a sterile formulation. In this case, sterilization of the composition according to the invention may be accomplished by passing the formulation, e.g. a formulated stock solution, through a sterile filter with a nominal pore size of 0.2 μm into a cleaned and sterilized container.

Thus, the method of the invention also may comprise a step of sterilizing the liquid formulation and a step of filling the formulation into sterile containers and capping the containers.

The composition according to the invention may be provided as a ready-to-use injection solution, wherein a liquid formulation of the invention, e.g. a stock solution, is brought to the desired volume by addition of one or more pharmaceutically acceptable solvents, such as selected from the group consisting of WFI, a glucose solution, electrolyte solution containing amino acids, lipids, vitamins, and other minerals, Ringer's solution, Hartmann's solution, or a sodium chloride solution in the form of an isotonic, hypotonic or hypertonic solution. An example of such pharmaceutically acceptable solution is Baxter Viaflo 9 mg/ml.

In one embodiment, an additional biologically active compound or agent can be present in or added to the composition according to the invention. For example, in case the formulation according to the invention is to be administered as an infusion fluid, an additional therapeutically active ingredient may be added to the fluid prior to administration to the patient. Examples of such therapeutically active ingredients are conventional cytostatics, particularly cisplatin, daunorubicin, cerubidine, cytarabine and fludarabine.

The composition of the invention is useful for the treatment of a disorder selected from hyperproliferative diseases, autoimmune diseases and heart diseases. An example of hyperproliferative disease is cancer. For the purpose of the present invention, examples of autoimmune diseases are scleroderma and rheumatoid arthritis and an example of heart disease is myocardial infarction.

In the PCT applications WO05/090341, WO04/084893, WO02/024692 and WO03/07025, incorporated herein by reference, the therapeutic activity of compounds of formula (I) has been demonstrated.

Thus, in WO02/024692 and WO03/07025, the use of compounds of formula (I) in the treatment of e.g. mutant p53 mediated cancers is disclosed. Examples of such cancers are osteosarcoma, lung adenocarcinoma, Burkitt's lymphoma, ovarian carcinoma, and colon carcinoma. By virtue of their ability to restore the apoptosis-inducing function of p53, compounds of formula (I) are also believed to be useful in treating other mutant p53 mediated diseases, such as, for example autoimmune diseases, such as rheumatoid arthritis and Sjogren's syndrome (e.g. Yamanishi Y. et al., Proc. Natl. Acad. Sci. USA 99(15):10025-30 (2002), Inazuka M. et al., Rheumatology, 39(3):262-6 (2000), Firestein G. S. et al., Proc. Natl. Acad. Sci. USA 30; 94(20):10895-900 (1997), and Tapinos N. I. et al., Arthritis Rheum. 42(7):1466-72 (1999)), and heart diseases such as hereditary idiopathic cardiomyopathy (e.g. Gudkova A. Ya. et al. in Identification of the TP53 tumor suppressor mutations in patients with family idiopathic cardiomyopathy. Abstract at the International Congress of the European Society of Pathology, May 19-21, 2002, Baveno, Lago Maggiore, Italy).

WO04/084893 discloses the use of compounds of formula (I), e.g. 2,2-bis(hydroxymethyl)quinuclidin-3-one, in the treatment of malignant melanoma and pathological conditions involving undesired angiogenesis.

In WO05/090341, the antiproliferative and apoptosis inducing effects of a compounds of formula (I) was shown, in an in vitro assay using a human lung carcinoma cell line.

The therapeutic activity of the compound 2-(hydroxymethyl)-2-(methoxymethyl)-quinuclidin-3-one (herein also referred to as APR-246) in the treatment of various cancers has been shown by in vitro assays using various cancer cell lines, cf. Table 2, wherein the $IC_{50}$ of APR-246 in various types of cancerous cells is shown.

TABLE 2

Effect of APR-246 on cell viability in various cancer cell lines

| Type of cancer | Cell type | $IC_{50}$ (µM) |
| --- | --- | --- |
| Osteosarcoma | SaOS-2 | 27 ± 5 (n = 35) |
| Osteosarcoma | SaOS-2-His273 | 14 ± 3 (n = 37) |
| Osteosarcoma | U-2OS | 15 ± 4 (n = 5) |
| Breast ductal carcinoma | BT-474 | 3 ± 2 (n = 2) |
| Breast adenocarcinoma | MCF-7 | 15 ± 1 (n = 3) |
| Breast adenocarcinoma | MDA-MB-231 | 18 ± 5 (n = 6) |
| Prostate adenocarcinoma | PC3-puro | 27 ± 3 (n = 3) |
| Prostate adenocarcinoma | PC3-175 | 23 ± 7 (n = 3) |
| Prostate carcinoma | 22Rv1 | 10 ± 0.6 (n = 3) |
| Colorectal adenocarcinoma | HT-29 | 25 ± 5 (n = 6) |
| Non-small cell lung carcinoma | H1299 | 16 ± 7 (n = 6) |
| Non-small cell lung carcinoma | H1299-His175 | 14 ± 8 (n = 6) |
| Acute Myelomonocytic Leukaemia | KBM3 | 7 ± 1 (n = 6) |

In Table 2, the results are shown as mean±SD; the $IC_{50}$ values are calculated as the average of the $IC_{50}$ values in the individual experiments.

Also in vivo studies indicate that the compounds of formula (I) have a pronounced anti-cancer activity. Thus, in vivo xenograft experiments in mice have shown that compounds of formula (I) have a significant anti-cancer effect. Indeed, in vivo xenograft experiments with mutant p53 osteosarcoma cells SaOS-2-His273 (FIG. 1) demonstrated a statistically significant anti-cancer effect has been shown for compounds of the invention.

Furthermore, in vivo experiments using the hollow fiber mouse model with 2-(hydroxymethyl)-2-(methoxymethyl) quinuclidin-3-one indicate that inventive compounds have a significant anti-leukemic effect. These experiments were performed using the hollow fiber in vivo mouse model (for a short description of the model, cf. the internet website http://dtp.nci.nih.gov/timeline/noflash/milestones/M13_hollow_fiber.htm).

Figure 2:
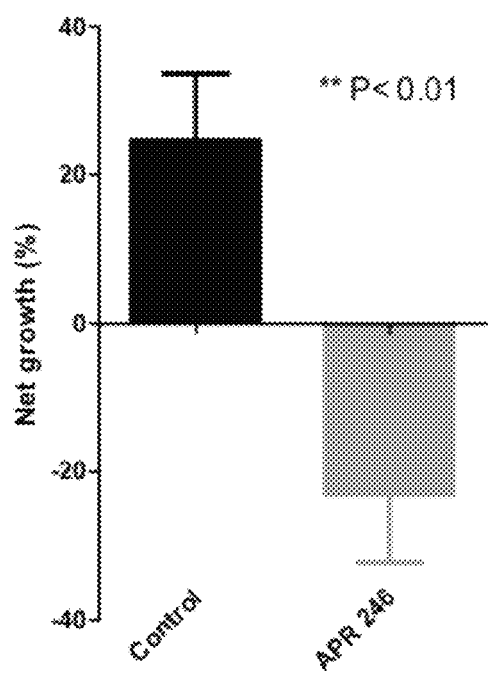
FIG. 2. shows the effect of APR-246 on AML MV-4-11 cells in the hollow fiber in vivo model. Data is shown as mean±SEM (n=7-8).

As shown in FIG. 2, at the end of the experiment the net growth of leukemic cells (AML MV-4-11 cells) was about 25% (by number) in mice treated with vehicle only (control). On the other hand, in mice treated with the inventive compound, the net growth of leukemic cells was about −25% by the end of the experiment, i.e. the number of leukemic cells had effectively decreased.

In view of the above data, it is contemplated that the composition of the present invention will be of use in the treatment of various disorders as mentioned herein above, e.g. osteosarcoma, lung adenocarcinoma, Burkitt's lymphoma, ovarian carcinoma, colon carcinoma, malignant melanoma, osteosarcoma, breast ductal carcinoma, prostate adenocarcinoma, prostate carcinoma, colorectal adenocarcinoma, non-small cell lung carcinoma, leukaemia, acute myelomonocytic leukaemia, autoimmune diseases, such as rheumatoid arthritis and Sjogren's syndrome; and heart diseases such as hereditary idiopathic cardiomyopathy.

EXAMPLES

Herein below, specific examples of the invention will be explained in more detail and specific examples will be provided according to the invention, which only serve to illustrate the invention, but are not to be considered as limiting in any way the scope of the invention.

Example 1

Stability Studies of APR-246 in an Aqueous System at Different pH

Several aqueous formulations of APR-246 and of the hydrochloric acid addition salt of APR-246 were prepared and tested for stability. APR-246 is readily soluble in water solutions, and the pKa of APR-246 gives alkaline water solutions with a pH of approximately 9 to 9.5.

It was observed that APR-246 suffered from degradation in aqueous solutions not only at room temperature but also at lower temperatures regardless of the concentration profile.

During the formulation development it was found that the stability of APR-246 in solution is dependent of pH and temperature. The stability increases with decreased pH. To establish a suitable pH for APR-246 with respect to stability, studies with the drug substance in different solutions at different pH were performed.

The summarised results are presented in Table 3. Under these model systems, formulations with pH above 6 showed stability problems. The HPLC analyses further revealed new peaks representing degradation products of APR-246.

TABLE 3

APR-246 content [%] in solution at different pH after 48 hours

| | pH 4 | | pH 5 | | pH 6 | | pH 7 | | pH 9 | |
|---|---|---|---|---|---|---|---|---|---|---|
| | \ | | | | Temperature | | | | | |
| | 4° C. | 25° C. | 4° C. | 25° C. | 4° C. | 25° C. | 4° C. | 25° C. | 4° C. | 25° C. |
| 80-120 mg/ml in water | 99.4 | 99.3 | 99.2 | 99.0 | 98.6 | 93.0 | 92.4 | 89.5[1] | 89.1 | 88.9[2] |
| 18 mg/ml in saline | 99.6 | 99.5 | 99.3 | 99.3 | 98.0 | 92.6 | 88.7 | 88.5[1] | 86.8 | 88.1[3] |

[1]Study discontinued after 12 hours;
[2]study discontinued after 9 hours;
[3]study discontinued after 6 hours.

Example 2

Stability Studies of APR-246 in Buffer System

To further elucidate the stability in aqueous solution and to evaluate the need for the solution to be buffered, studies with APR-246 in saline with and without citrate buffer have been performed. The summarised results are presented in Table 4. The results indicate that degradation increases with pH and temperature. It also is shown that the solution does not need to be buffered; pH is sufficiently stable without buffer.

TABLE 4

Stability of APR-246 in solution with and without buffer

| | | HPLC (area % of main component, not adjusted for blank) | | | | | |
|---|---|---|---|---|---|---|---|
| | | | 40° C. | | | | 25° C. |
| Formulation | Start | 1 w | 2 w | 3 w | 4 w | 4 w |
| A: NaCl (9 mg/mL) HCl (pH 4) | 96% | 95% | 93% | 93% | 94% | 96% |
| B: NaCl (9 mg/mL) Na-citrate 25 mM (pH 4.5) | 94%[1] | 83%[1] | 87%[1] | 88%[1] | 87%[1] | 94%[1] |
| C: NaCl (9 mg/mL) Na-citrate 25 mM (pH 4) | 94%[1] | 92%[1] | 92%[1] | 92%[1] | 91%[1] | 95%[1] |

[1]Citrate buffer peak elutes at same time as degradation peak 2

Based on the combined results of these studies, it is concluded that an aqueous WFI stock solution of APR-246 with a saline concentration between 0.5% and 1.0% and with a pH range between pH 3.5 and pH 4.5, e.g. pH 4, is advantageous for clinical formulation.

It was further concluded from the described model system that the standard formulations are sensitive to normal thermal sterilization. Instead the sterilization was performed by filtering the final product formulation through a sterile filter with a nominal pore size of 0.2 μm into a cleaned and sterilized container. The so sterilized solution may then be dispensed into clean sterile depyrogenated glass vials of an appropriate size prior to capping of the vials. The manufacturing was in compliance with current Good Manufacturing Practices regulations.

Example 3

Long Term Stability Studies of APR-246 in Aqueous System

APR-246 stock solutions were manufactured at a concentration of about 150 mg/mL at pH 3.9. The finished product consisted of 21.5-22.0 mL of drug product aseptically filled into presterilized 50 mL glass vials. The manufacturing was in compliance with Good Manufacturing Practices regulations. The summarized results of two batches are presented in Table 5.

TABLE 5

Stability test of APR-246 (150 mg/mL) in aqueous system at pH 3.9-4.0

| | | | \multicolumn{7}{c}{Content of APR-246 in solution [%]} | | | | | | |
|---|---|---|---|---|---|---|---|---|
| Batch No | Temp (° C.) | Initial | 1 month | 3 months | 6 months | 9 months | 12 months | 24 months |
| 1 | 5° C. | 99.5 | 99.6 | 99.3 | 99.4 | 99.3 | 99.3 | 98.9 |
| 1 | 25° C. | 99.5 | 99.2 | 98.7[1] | 97.2[1] | n.a. | 96.3[1] | Discont. |
| 1 | 40° C. | 99.5 | 97.2 | 94.0[1] | | Discontinued[1] | | |
| 2 | 5° C. | 99.8 | 99.5 | 99.7 | 99.6 | 99.6 | 99.6 | na |
| 2 | 25° C. | 99.8 | 99.2 | 98.6[1] | 98.0[1] | 98.0[1] | Discontinued[1] | |

[1]Formation of solids.
n.a. not analyzed

The long term stability data for APR-246 formulated as described herein for clinical use indicate that APR-246 is stable in the inventive formulation, and it is expected that there will be no significant degradation over a period of two years when the product is stored at 2-8° C.

Example 4

Formulation of a Stable APR-246 Stock Solution Containing 150 mg/mL at pH 3.9

To a mixture of aqueous HCl (1890 g, 5.03M) and WFI (7960 g) in a 25 L sterilized container equipped with a pH probe for monitoring of the pH, was added NaCl (105 g) while stirring at room temperature. When the NaCl was fully dissolved, APR-246 (1747 g) was added in portions to the stirred solution resulting in a pH of 4.75. Aqueous HCl (11.1 mL, 5.03 M) was added in small portions resulting in pH adjustment to pH 4.0. APR-246 (3.0 g) was finally added to the mixture and the resulting pH 4.40 was adjusted to pH 3.9 by careful addition of aqueous HCl (3.5 mL, 5.03M). Finally WFI (484 g) was added to the mixture while stirring for an additional 5 min.

The stock solution was filtered through an Opticap XL4 filter (1.0/0.5 μm) to clean glass containers and then further filtered through a Kleenpak KA1 filter (0.22 μm) into a sterile container (class B area). Dispensing of the sterile vials and capping with sterile stoppers/caps was performed under aseptic conditions (class A area). The filters were tested for integrity and samples (vials) from the production were taken for assay and sterile analyses as well as for stability testing. Several batches using the herein described protocol were manufactured with assay and sterile analyses well within the specified limits.

Example 5

Analytical Methods

HPLC—Chromatography was performed on an Agilent 1100/1200 series HPLC system using a Purospher Star RP-18e, 5 μm (250×4.6) mm Column at 20° C. Sample temperature was set to 5° C. by a thermostat. Detection was accomplished by means of a UV/VIS DAD detector at 210 nm. The flow rate was set to 1.0 mL/min and the injection volume was 10 μL. The mobile phase used was a gradient of phosphate buffer (A) in acetonitrile (B): 0-5 min: 90% A, 5-20 min: 70% A, 20-35 min: 20% A, 35-45 min: 90% A. The calibration was obtained using pure APR-246 standard solutions freshly prepared prior to analyses. Data acquisition was performed electronically. The method has been validated.

Example 6

Microbiological Attributes

The APR-246 drug product was a sterile concentrate for solution for infusion. The solution was sterilised by filtration according to Ph Eur standard method and aseptically filled in vials. The possibility to autoclave the solution in the final container was investigated, but degradation was too pronounced to enable that process. The summarized results of two batches sterilized at 121° C. are presented in Table 6.

TABLE 6

HPLC-UV results before and after autoclaving (121° C., 20 min) of APR-246 solution 150 mg/ml, pH 4.0 and 4.5 respectively

| pH 4.0 | | pH 4.5 | |
|---|---|---|---|
| APR-246 (%) initial | APR-246 (%) After sterilization | APR-246 (%) initial | APR-246 (%) After sterilization |
| 94.3 | 86 | 94 | 78.5 |

Example 7

Infusion Bag Compatibility

This example summarizes the results of a compatibility study of the APR-246 drug product (150 mg/mL stock solution) in six infusion bags, to confirm physical and chemical stability of the drug product in the NaCl solution and compatibility with infusion bags and tubing device material. The drug product should be diluted with sterile 0.9% NaCl solution for infusion to a total volume of 500 ml before administration.

The duration of the study covers a period beyond finalisation of infusion to the patient. The study was designed for a worst case lowest dose of 0.15 mg/mL and for a worst case highest dose of 24 mg/mL.

The important factor for the interaction of drug and infusion system is the relationship between the surface of the infusion bag and drug amount (mg/cm$^2$) and the lowest drug concentration represents the most accelerated case for a compatibility study. The high concentration was included to cover the range of doses and to elucidate the pH of the final solution for infusion over this dosage range.

The study was performed at room temperature using Baxter Infusion bags (Viaflo) lot no 08F22E1C. The scheduled design is presented in Table 7.

TABLE 7

| | Sample design | |
|---|---|---|
| Sample ID | Sampling | Sample |
| A | day 0 | 150 mg/ml |
| X | day 0 | infusion liquid |
| B | 9:30 | Infusion bag |
| C | 12:00 | Infusion bag |
| D | 14:30 | after 30 min in tube |
| E | 17:00 | after 30 min in tube |
| F | 07:30 | after 30 min in tube |

Three infusion bags for each concentration, "high" and "low" were prepared. One infusion bag per day was studied and prepared freshly from the refrigerated APR-246 stock solution.

Low Concentration

The results are presented in Table 8 and show a satisfactory stability over the range of the study.

TABLE 8

| | Assay of low concentration | | | | | |
|---|---|---|---|---|---|---|
| | | Assay APR-246 [mg/mL] | | | pH | |
| Sample ID | Time (h) | Low1 | Low2 | Low3 | Low1 | Low2 | Low3 |
| Low B | 0.00 | n.a. | 0.179 | 0.168 | 5.7 | 5.7 | 5.8 |
| Low C | 2.50 | 0.174 | 0.179 | 0.167 | 5.7 | 5.6 | 5.7 |
| Low D | 5.00 | 0.173 | 0.179 | 0.167 | 5.8 | 5.6 | 5.8 |
| Low E | 7.50 | 0.171 | 0.179 | 0.166 | 5.6 | 5.6 | 5.7 |
| Low F | 22.00 | 0.170 | 0.179 | 0.165 | 5.6 | 5.6 | 5.7 |
| RSD[1] | | 1.3% | 0.2% | 0.6% | | | |
| Assay decrease | | 2% | 0% | 2% | | | |

[1]The relative standard deviation (RSD) is based on the bag average values from samples B-F (except from Low 1, where the value is based on C-F).
n.a. not analyzed High Concentration The results are presented in Table 9 and show a satisfactory stability over the range of the study.

TABLE 9

| | Assay and pH of high concentration | | | | | |
|---|---|---|---|---|---|---|
| Sample ID | Time (h) | Assay APR-246 [mg/mL] | | | pH | |
| | | High1 | High2 | High3 | High1 | High2 | High3 |
| High B | 0.00 | 20.706 | 21.023 | 20.671 | 4.4 | 4.2 | 4.2 |
| High C | 2.50 | 22.295 | 22.582 | 22.114 | — | 4.2 | 4.2 |
| High D | 5.00 | 22.173 | 22.532 | 22.101 | 4.3 | 4.2 | 4.2 |
| High E | 7.50 | 22.163 | 22.506 | 22.509 | — | 4.1 | 4.2 |
| High F | 22.00 | 22.415 | 22.531 | 21.858 | 4.2 | 4.3 | 4.2 |
| RSD[1] | | 0.5% | 0.1% | 1.2% | | | |
| Assay decrease | | 0% | 0% | 1% | | | |

[1]The relative standard deviation (RSD) is based on the bag average values from samples C-F.

Together, the tables show that the low and high concentration infusion bag solutions prepared from the 150 mg/mL APR-246 liquid formulation are stable over at least 22 hours.

Thus, this example indicates that a liquid formulation of the invention may be used to prepare a parenterally administrable, diluted solution having an adequate stability that allows it to be manipulated and administered in a practical and safe manner.

As has been shown herein above, by the present invention, a storage-stable liquid composition comprising a compound according to formula (I) as defined herein, or a pharmaceutically acceptable salt thereof, is provided.

The invention claimed is:

1. A liquid composition, comprising an aqueous solution of a compound of formula (I)

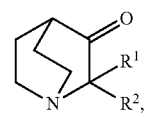

(I)

or a pharmaceutically acceptable salt thereof, and
a pH regulating agent,
wherein:
$R^1$ is selected from H, —$CH_2$—O—$R^3$, —$CH_2$—S—$R^3$, and —$CH_2$—$NR^3R^4$;
$R^2$ is selected from —$CH_2$—O—$R^3$, —$CH_2$—S—$R^3$, and —$CH_2$—$NR^3R^4$; and
$R^3$ and $R^4$ are the same or different and are independently selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C2-C10 heteroaryl or non-aromatic C2-C10 heterocyclyl containing one or several heteroatoms independently selected from N, O and S; or
$R^3$ and $R^4$ in —$CH_2$—$NR^3R^4$ are bonded together and form, together with the nitrogen atom to which they are bonded, a substituted or non-substituted non-aromatic C2-C10 mono- or bicyclic heterocyclyl optionally containing one or more further heteroatoms independently selected from N, O and S and optionally comprising one or more cyclic keto groups;
wherein the substituents of the substituted groups are independently selected from unbranched or branched, saturated or unsaturated C3-C12 cycloalkyl or C1-C10 alkyl; halogen; halogen-substituted C1-C10 alkyl, mono- or bicyclic aryl; mono-, bi- or tricyclic C2-C10 heteroaryl or non-aromatic C2-C10 heterocyclyl containing one or several heteroatoms independently selected from N, O and S; C1-C10 alkoxy; amino; and C1-C10 alkylamino;
wherein the aqueous solution has a pH from 3.0 to 5.0.

2. The liquid composition according to claim 1, wherein $R^1$ is selected from H and —$CH_2$—O—$R^3$; and $R^2$ is —$CH_2$—O—$R^3$.

3. The liquid composition according to claim 1, wherein each $R^3$ is independently H or substituted or non-substituted, unbranched or branched, saturated or unsaturated C1-C6 alkyl.

4. The liquid composition according to claim 3, wherein each $R^3$ is independently H or methyl.

5. The liquid composition according to claim 4, wherein the compound is 2-(hydroxymethyl)-2-(methoxymethyl)quinuclidin-3-one or 2,2-bis(hydroxymethyl)-quinuclidin-3-one.

6. The liquid composition according to claim 1, further comprising at least one additional therapeutically active agent.

7. The liquid composition according to claim 1, wherein the aqueous solution has a pH between 3.0 and 4.5.

8. The liquid composition according to claim 1, wherein the compound of formula (I) is present in the aqueous solution at a concentration of from 10 mg/mL to 250 mg/mL.

9. The liquid composition according to claim 1, wherein the aqueous solution comprises NaCl at a concentration of between 0% to 3% weight by volume.

10. The liquid composition according to claim 1, for use in the treatment of a disorder selected from hyperproliferative diseases, autoimmune diseases and heart diseases.

11. A method for preparing the liquid composition according to claim 1, comprising adding, to an aqueous phase,
the compound of formula (I), or a pharmaceutically acceptable salt thereof;
optionally, at least one further therapeutically active agent; and
a pH regulating agent in an amount so as to provide a pH in the composition of from 3.0 to 5.0.

12. The method according to claim 11, wherein the pH regulating agent is added in an amount so as to provide a pH in the composition of from 3.0 to 4.5.

13. The method according to claim 11, wherein NaCl is added to the aqueous phase in an amount so as to provide a concentration of NaCl in the liquid composition of up to 3% weight by volume.

14. The method according to claim 11, wherein the compound of formula (I), or the pharmaceutically acceptable salt thereof, is added to the aqueous phase in an amount so as to provide a concentration of the compound of formula (I) in the liquid composition of from 10 mg/mL to 250 mg/mL.

15. The liquid composition according to claim 1, wherein the compound is 2-(hydroxymethyl)-2-(methoxymethyl)quinuclidin-3-one.

16. The liquid composition according to claim 1, wherein the compound is selected from the group consisting of:
2-[(benzyloxy)methyl]quinuclidin-3-one;
2-(butoxymethyl)quinuclidin-3-one;
2-(propoxymethyl)quinuclidin-3-one;
2-[(phenylthio)methyl]quinuclidin-3-one;
2-[(7H-purin-6-ylthio)methyl]quinuclidin-3-one;
2-(2,3-dihydro-1H-indol-1-ylmethyl)quinuclidin-3-one;
2-({[2-amino-3-chloro-5-(trifluoromethyl)phenyl]-amino}methyl)quinuclidin-3-one;
2-(morpholin-4-ylmethyl)quinuclidin-3-one;
2-[(4-methylpiperazin-1-yl)methyl]quinuclidin-3-one;
2-{[ethyl(pyridin-4-ylmethyl)amino]methyl}quinuclidin-3-one;
2-[(3,5-dimethylpiperazin-1-yl)methyl]quinuclidin-3-one;
2-[(5,6-dimethyl-1H-benzimidazol-1-yl)methyl]-quinuclidin-3-one;
2-[(7-amino-1H-[1,2,3]triazolo[4,5-d]pyrimidin-1-yl)methyl]quinuclidin-3-one;
1,3-dimethyl-7-[(3-oxo-1-azabicyclo[2.2.2]oct-2-yl)-methyl]tetrahydro-1H-purine-2,6,8(3H)-trione;
2-[(2,6-dichloro-9H-purin-9-yl)methyl]quinuclidin-3-one; and
2-[(6-methoxy-9H-purin-9-yl)methyl]quinuclidin-3-one 17. A concentrated stock solution, comprising an aqueous solution of a compound of formula (I)

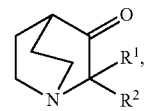

(I)

or a pharmaceutically acceptable salt thereof,
and a pH regulating agent,
the compound of formula (I) being present in the stock solution at a concentration of 75 mg/mL to 250 mg/mL, and the stock solution having a pH of from 3.8 to 4.2,
wherein:
$R^1$ is selected from H, —$CH_2$—O—$R^3$, —$CH_2$—S—$R^3$, and —$CH_2$—$NR^3R^4$;
$R^2$ is selected from —$CH_2$—O—$R^3$, —$CH_2$—S—$R^3$, and —$CH_2$—$NR^3R^4$; and
$R^3$ and $R^4$ are the same or different and are independently selected from H; substituted or non-substituted, unbranched or branched, saturated or unsaturated C3-C12 cycloalkyl or C1-C10 alkyl; substituted or non-substituted benzyl; substituted or non-substituted mono- or bicyclic aryl; substituted or non-substituted mono-, bi- or tricyclic C2-C10 heteroaryl or non-aromatic C2-C10 heterocyclyl containing one or several heteroatoms independently selected from N, O and S; or
$R^3$ and $R^4$ in —$CH_2$—$NR^3R^4$ are bonded together and form, together with the nitrogen atom to which they are bonded, a substituted or non-substituted non-aromatic C2-C10 mono- or bicyclic heterocyclyl optionally containing one or more further heteroatoms independently selected from N, O and S and optionally comprising one or more cyclic keto groups;
wherein the substituents of the substituted groups are independently selected from unbranched or branched, saturated or unsaturated C3-C12 cycloalkyl or C1-C10 alkyl; halogen; halogen-substituted C1-C10 alkyl, mono- or bicyclic aryl; mono-, bi- or tricyclic C2-C10 heteroaryl or non-aromatic C2-C10 heterocyclyl containing one or several heteroatoms independently selected from N, O and S; C1-C10 alkoxy; amino; and C1-C10 alkylamino,
and wherein the stock solution is storage stable.

18. The concentrated stock solution according to claim 17, wherein the stock solution further comprises NaCl at a concentration of between 0.5% to 1.5% weight by volume.

19. The concentrated stock solution according to claim 17, wherein said pH regulating agent comprises a pharmaceutically acceptable organic acid or inorganic mineral acid, a pharmaceutically acceptable acid buffer, or any mixture thereof.

* * * * *